US012727948B2

(12) United States Patent
Long et al.

(10) Patent No.: US 12,727,948 B2
(45) Date of Patent: Sep. 8, 2026

(54) ADVANCED TRACKING ARRAY

(71) Applicant: DEPUY IRELAND UNLIMITED COMPANY, Co Cork (IE)

(72) Inventors: William J. Long, New York, NY (US); Daniel Girardeau-Montaut, Grenoble (FR)

(73) Assignee: DEPUY IRELAND UNLIMITED COMPANY, Co Cork (IE)

( * ) Notice: Subject to any disclaimer, the term of this patent is extended or adjusted under 35 U.S.C. 154(b) by 70 days.

(21) Appl. No.: 18/063,611

(22) Filed: Dec. 8, 2022

(65) Prior Publication Data

US 2024/0189040 A1 Jun. 13, 2024

(51) Int. Cl.
*A61B 34/20* (2016.01)
*A61B 90/00* (2016.01)
*G06T 7/73* (2017.01)

(52) U.S. Cl.
CPC ................ *A61B 34/20* (2016.02); *G06T 7/73* (2017.01); *A61B 2034/2055* (2016.02); *A61B 2034/2065* (2016.02); *A61B 2034/2072* (2016.02); *A61B 2090/3937* (2016.02); *G06T 2207/20061* (2013.01); *G06T 2207/20081* (2013.01); *G06T 2207/30204* (2013.01)

(58) Field of Classification Search
CPC ............ A61B 34/20; A61B 2034/2055; A61B 2034/2065; A61B 2034/2072; A61B 2090/3937; G06T 7/73; G06T 2207/20061; G06T 2207/20081; G06T 2207/30204
See application file for complete search history.

(56) References Cited

U.S. PATENT DOCUMENTS

| | | | | |
|---|---|---|---|---|
| 6,787,750 | B1 * | 9/2004 | Sauer | G06T 7/73 250/559.4 |
| 10,039,607 | B2 * | 8/2018 | Heigl | A61B 90/39 |
| 2018/0235566 | A1 * | 8/2018 | Tamersoy | A61B 6/4458 |
| 2019/0001156 | A1 * | 1/2019 | Tulik | A61N 5/1081 |
| 2019/0388099 | A1 * | 12/2019 | Zuhars | A61B 34/10 |
| 2020/0197107 | A1 * | 6/2020 | Ryan | A61B 90/361 |
| 2020/0390506 | A1 * | 12/2020 | Bonny | A61B 34/25 |
| 2021/0186355 | A1 * | 6/2021 | Ben-Yishai | A61B 34/10 |
| 2021/0401510 | A1 * | 12/2021 | Theodore | A61B 34/20 |
| 2022/0110701 | A1 * | 4/2022 | Crawford | A61B 34/76 |
| 2024/0041558 | A1 * | 2/2024 | Siewerdsen | A61B 90/94 |

OTHER PUBLICATIONS

Juan Manuel Rivas Diaz; "Model-Based Object Tracking with an Infrared Stereo Camera"; Studies from the Department of Technolgy at Orebro University; 2015.

* cited by examiner

*Primary Examiner* — Sean A Frith
(74) *Attorney, Agent, or Firm* — Kramer & Amado, P.C.

(57) ABSTRACT

A tracking array tracking system, including: at least one processor; and at least one memory storing instructions, that when executed by the at least one processor, cause the tracking array system at least to: determine that one marker of a plurality of markers on a tracking array is obstructed to a camera system; identify marker lines on the tracking array; determine a location of the marker lines of the tracking array; and determine a location and orientation of the tracking array based upon the location of the marker lines.

21 Claims, 5 Drawing Sheets

300
304
322
322
302
322
322

200
212
222
204
212
202
222
212

ADVANCED TRACKING ARRAY

TECHNICAL FIELD

Various exemplary embodiments disclosed herein relate generally to advanced tracking arrays for use in computer-aided surgery (CAS).

BACKGROUND

Tracking arrays are used in computer-aided surgery to track the location of the patient, surgical tools, and in some cases surgical robots. A camera system provides the ability to determine the location of the tracking arrays relative to one another. This location information may then be used by the surgeon carrying out the computer-aided surgery.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a tracking array tracking system, including: at least one processor; and at least one memory storing instructions, that when executed by the at least one processor, cause the tracking array system at least to: determine that one marker of a plurality of markers on a tracking array is obstructed to a camera system; identify marker lines on the tracking array; determine a location of the marker lines of the tracking array; and determine a location and orientation of the tracking array based upon the location of the marker lines. The tracking array tracking system of claim 1, wherein the instructions further cause the tracking array system at least to: determine a location of the plurality of marker on the tracking array; and determine a location and orientation of the tracking array based upon the location of the plurality of marker.

Various embodiments are described, wherein identifying marker lines includes using a Hough Transform.

Various embodiments are described, wherein identifying marker lines includes using a binarization process with a skeletonization process.

Various embodiments are described, wherein identifying marker lines includes using a machine learning pattern matching model.

Various embodiments are described, wherein determining location and orientation of the tracking array includes: determining the location of an intersection of marker lines proximate the obstructed reflective element; and determining the location of the obstructed reflective element based upon the location of the intersection of the marker lines.

Various embodiments are described, wherein the marker lines are curved.

Fvewrta method for tracking a tracking array in a computer aided surgery system, including: determining that one reflective element of a plurality of marker on the tracking array is obstructed to a camera system; identifying marker lines on the tracking array; determining a location of the marker lines of the tracking array; and determining a location and orientation of the tracking array based upon the location of the marker lines.

Various embodiments are described, further including: determining a location of the plurality of marker on the tracking array; and determining a location and orientation of the tracking array based upon the location of the plurality of marker.

Various embodiments are described, wherein identifying marker lines includes using a Hough Transform.

Various embodiments are described, herein identifying marker lines includes using a binarization process with a skeletonization process.

Various embodiments are described, wherein identifying marker lines includes using a machine learning pattern matching model.

Various embodiments are described, wherein determining location and orientation of the tracking array includes: determining the location of an intersection of marker lines adjacent the obstructed reflective element; and determining the location of the obstructed reflective element based upon the location of the intersection of the marker lines.

Various embodiments are described, wherein the marker lines are curved.

Further various embodiments relate to a method for tracking a tracking array in a computer aided surgery system, including: identifying marker lines on the tracking array; determining a location of the marker lines of the tracking array; and determining a location and orientation of the tracking array based upon the location of the marker lines.

Various embodiments are described, wherein identifying marker lines includes using a Hough Transform.

Various embodiments are described, wherein identifying marker lines includes using one of a binarization process with a skeletonization process and a machine learning pattern matching model.

Various embodiments are described, wherein determining location and orientation of the tracking array includes: determining locations of intersections of marker lines of the tracking array; and computing the location and orientation of the tracking array based upon the locations of the intersections of the marker lines of the tracking array.

BRIEF DESCRIPTION OF THE DRAWINGS

In order to better understand various exemplary embodiments, reference is made to the accompanying drawings, wherein embodiments of a device for use in computer-aided surgery are shown.

To facilitate understanding, identical reference numerals have been used to designate elements having substantially the same or similar structure and/or substantially the same or similar function.

DETAILED DESCRIPTION

Figures 1, 2:
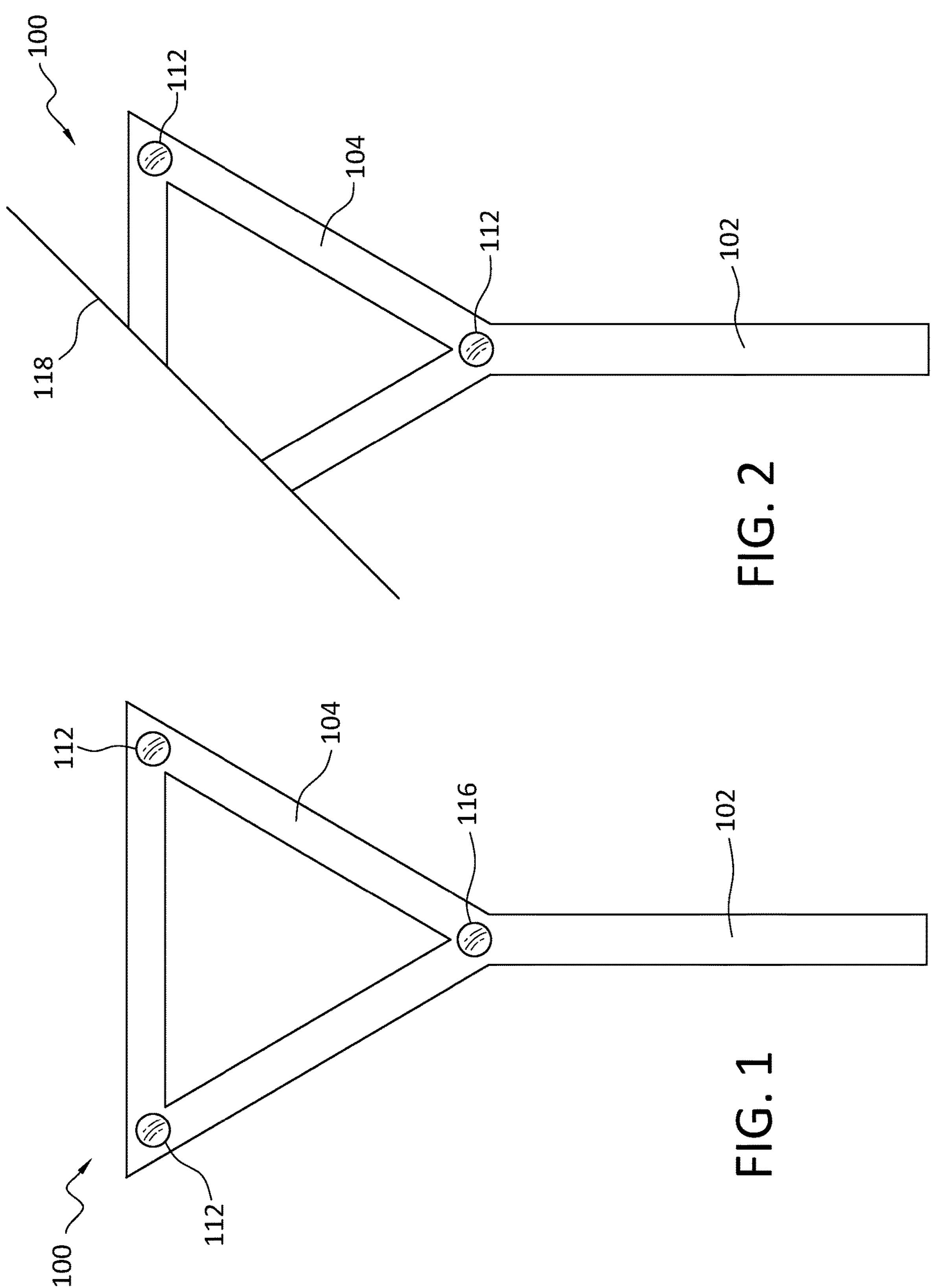
FIG. 1. illustrates an example of a tracking array.
FIG. 2 illustrates one of the reflective spheres being blocked by an obstruction.

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Before computer-aided surgery (CAS) surgery takes place, the CAS system may learn the locations and relationships of various elements like medical instruments (e.g., scalpel, saw, drill, bone screw, implant, robot, etc.) and the patient (based optionally on images of the patient which might be obtained by a fluoroscopy, x-ray, CT, MRI, etc.) To enable the CAS to locate the patient, the patient typically has a navigation array attached somewhere on their body, often attached to a bone for stability. These navigation arrays can be monitored by a location device or system such as a spatial camera, one of which is commercially available from Northern Digital Inc. Spatial cameras typically use an internal coordinate system that is defined by the camera, not by the location of the patient (the spatial camera can be placed in various locations relative to the patient). The navigation arrays may be an array of reflective elements such as reflective spheres that reflect light back to the spatial camera (the spatial camera or other light source might emit infrared (IR) light and then sense the IR light reflected back from the reflective spheres using stereoscopic cameras, and thereby being able to spatially locate the reflective spheres).

Many surgeries use imaging devices (e.g., fluoroscope, x-ray, CT, MRI) that take images of the patient which can be helpful to the surgeon during surgery. Fiducials, such as radiopaque markers, can be attached to the patient before the imaging occurs. These fiducials make relatively well-defined landmarks in the image which can be used later to transform between the patient coordinate system and the camera coordinate system. The imaging devices typically have their own internal coordinate system that is defined by the imaging device itself and has no fixed relation to the coordinate system of the spatial camera (the camera can typically be placed in various locations relative to the imaging device).

Navigation arrays can also be attached to surgical instruments so that the CAS system can track the spatial location of the instrument. The spatial camera tracks the location of the navigation array, and thus the surgical instrument in the coordinate system of the camera. But it is only part of the picture for the spatial camera to know the location of the surgical instrument in the camera coordinate system. It is helpful for the CAS system to be able to know where the instrument is relative to the patient.

To accomplish this, various processes are used in setting up the CAS system before a surgery. One process is used to allow the CAS system to harmonize between the spatial camera coordinate system, the patient coordinate system, and/or the image device coordinate system—this process is typically called registration. In registration, the CAS system determines the relationship between the various coordinate systems. That is, if the CAS system knows the spatial relationship between navigation arrays connected to the patient (which are monitored by the spatial camera) and the fiducials connected to the patient (which show up in the images created by the imaging device), the CAS system can relate that information mathematically/spatially so that the image of the patient can be appropriately aligned with or overlaid onto the patient in 3D space. As an alternative to fiducials connected to the patient, for example, in imageless CAS systems, the CAS system prompts the surgeon to touch various anatomical landmarks on the patient with a navigated probe (or "pointer" as described in more detail below) to "teach" the CAS system the spatial location of the patient's anatomy.

The CAS system also needs to know the spatial relationship between the navigation array and the tip of the surgical instrument, as the tip is the part that may be altering the tissue of the patient. Another process is used to allow the CAS to obtain this relationship—this is typically called calibration. The term calibration may be used to describe the scenario in which the CAS system learns the distance or geometric relationship between the array and the tip of the tool, for example when the CAS system does not know the exact geometry of the surgical instrument. If the CAS system allows any length saw blade to be used, it can require the user to calibrate the tip of the blade. To accomplish this, the CAS system can use a "pointer" which is another surgical instrument with a pointed tip, a shaft, and a navigation array connected to the shaft such that the tip is located at a fixed location relative to the array. The CAS system is programmed to know this fixed geometric relationship and thus can use the pointer to obtain geometric points in 3D space, such as the tip of the saw blade (other points on the saw blade may be used such as divots on the saw blade that have a known relation to the tip of the saw blade) and can then deduce the relationship between the tip of the saw blade and the navigation arrays.

These processes harmonize the spatial relationships between the various elements of the CAS system. In this manner, the CAS system can know where the tip of the saw blade is relative to the patient, not just relative to the camera system, and images can be correlated to the actual position of the patient providing surgeons with information not available to the eye, such as the locations of bone or even nerves whose view is obstructed by the patient's skin.

FIG. 1 illustrates an embodiment of a tracking array. The tracking array 100 may include mount 102 and body 104. The mount 102 is connected to the body 104 and provides a mounting structure. The mount 102 may facilitate connecting the tracking array 100 to the patient, a tool, a robot, or any other item that needs to be tracked during the CAS. The mount 102 may also take any shape in order to facilitate the connection to the item to be tracked.

Three markers 112 may be attached to the body 104. The markers may be active elements such as an LED or other light source or passive elements that reflect light. In this embodiment the three markers are three markers 112 attached are attached to the body 104 as illustrated. While reflective spheres are illustrated, instead other reflective elements having other shapes may be used as well. The markers 112 are tracked by the camera as described above. The markers 112 are shown as attached to the body 104 near the corners of the body 104. The body 104 is shown as having a triangular shape to accommodate the three markers 112. The body 104 may take on other shapes as well. Further, the tracking array 100 may include more than three markers 112, and in such embodiments, the body 104 may take other shapes to accommodate different numbers of markers. The use of three markers 112 is common because this is the minimum number of markers that define a plane that may be used to determine the location and orientation of the tracking array and hence the tracked item to which the array is attached. If more than three markers 112 are used, then they may or may not be coplanar depending upon the specific application.

As the camera system may see multiple arrays, the camera system needs to be able to group markers 112 for each tracking array 100 together. This may be accomplished by markers 112 for each tracking array 100 having unique physical locations and parameters. For example, the spacing between the markers 112 may be unique for each tracking array 100. Further, the angles formed by the markers 112 may also be used to differentiate between different tracking arrays 100. The camera records at least two different images of the surgical scene in order to determine the three dimensional location of objects in the scene. The camera processes the received images to identify the different markers 112 that it sees. It then groups the markers 112 that belong to the same tracking array 100. At this point the locations of the tracking arrays 100 in the received images may be processed to determine the relative location of the tracking arrays 100.

It is noted that if the markers are active elements, then the markers for one array at a time may be turned on and the camera system will know which array it is viewing. Accordingly, the techniques described above for identifying specific tracking arrays may not be needed.

One problem that may arise during surgery is that one of the markers 112 may be blocked from the view of the camera system. FIG. 2 illustrates one of the markers 112 being blocked by an obstruction 118. In this case, there is not enough data to determine the precise location and orientation of the tracking array 100. For example, during surgery a surgical drape, a hand or arm of surgical personnel, a tool, a retractor, another array, etc. may obstruct the view of one of the markers 112. Embodiments of tracking arrays will now be described to overcome the problem of obstructing the view of the markers 112.

Figures 3, 4:
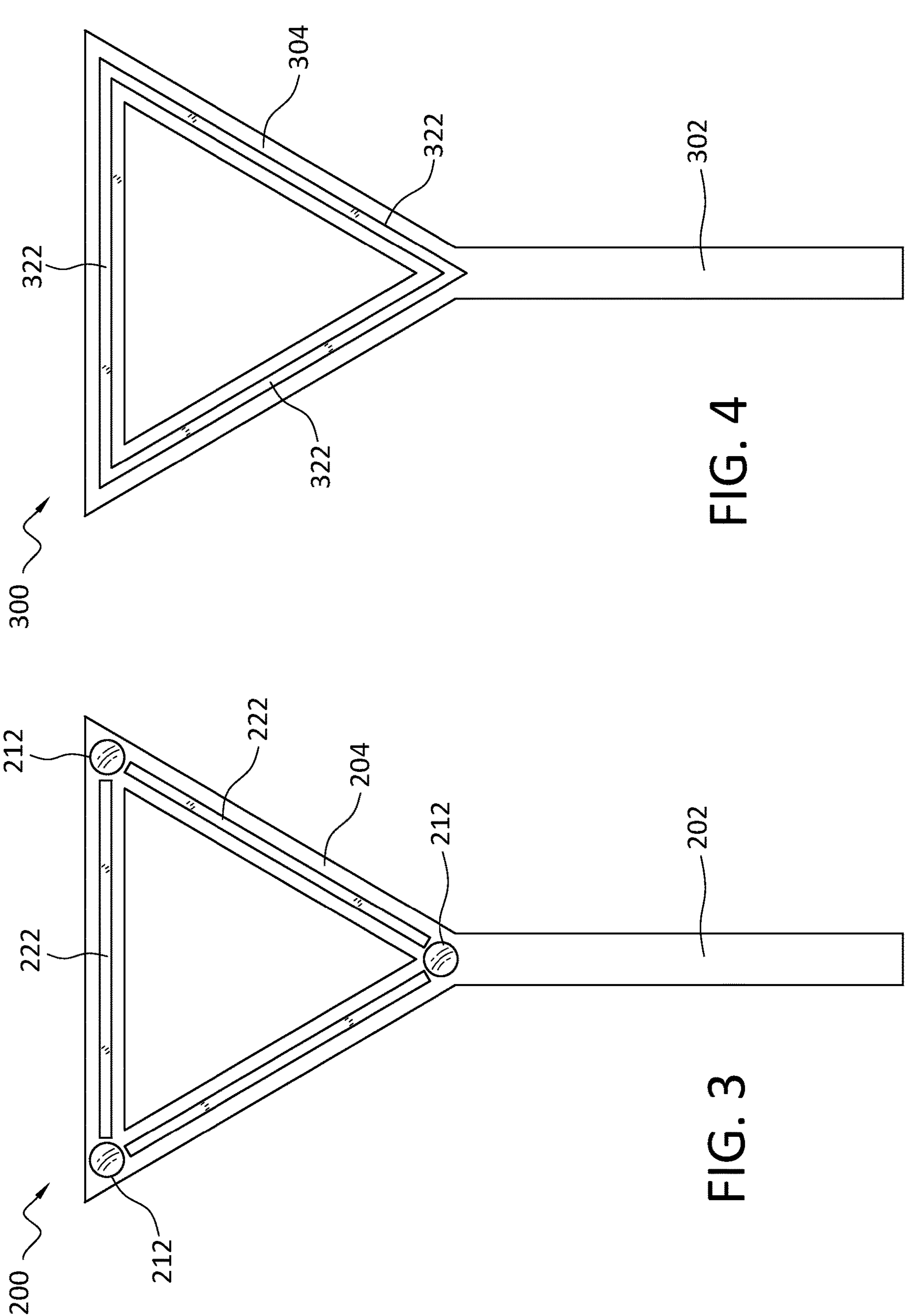
FIG. 3 illustrates an embodiment of a tracking array that may be used when part of the tracking array is obstructed.
FIG. 4 illustrates another embodiment of a tracking array that may be used when part of the tracking array is obstructed.

FIG. 3 illustrates an embodiment of a tracking array that may be used when part of the tracking array is obstructed. The tracking array 200 is similar to the tracking array 100 of FIG. 1 but adds marker lines 222 to the body 204 of the tracking array 200. The marker lines 222 may be reflective and may also have a specific color (i.e., that reflect light at specific frequencies that may be detected and associated with the marker lines). In other embodiments, the marker lines 22 may be active by emitting light. The tracking array 200 has a mount 202, body 204, and markers 212 similar to those of FIG. 1. As result when no obstruction is present, the camera system may use the markers 212 to determine the location and orientation of the tracking array 200 using normal methods. If one of the markers 212 is obstructed, then the marker lines 222 provide the ability to determine the location and orientation of the tracking array 200.

The marker lines 222 are shown as lines that extend between the markers 212. The marker lines 222 are made of a reflective material that reflects the light used to illuminate the tracking array 200. The reflective materials used for the marker lines 222 may be the same as that used for the markers 212. The marker lines 222 are also shown as intersecting at the location of the markers 212. In this geometry, the camera may process the images of the marker lines 222 and determine where they intersect. As the intersections of the marker lines 222 are at the locations of markers 212 (possibly with a small offset for example if the lines 222 do not intersect at the center of a sphere), that intersection point may then be used to determine the location of the blocked marker lines 222. Then this location may be used with the locations of the other visible marker lines 222 to determine the location and orientation of the tracking array 200. The same basic processing that is used when all the markers 212 are visible may then be used to determine the location and orientation of the tracking array 200. In an alternative embodiment, the marker lines 222 may not intersect at the locations of the markers 212, but the locations of these intersections relative to the locations of the markers 212 is known so that the location of the intersections of the marker lines 222 may be adjusted to reflect the location of the markers 212 which adjusted locations may then be used with the existing algorithms that process the locations of the markers 212.

It is further noted, that in situations when two or more of the markers 212 are blocked, that if a sufficient portion of the marker lines 222 are still visible and their orientation can be determined, then this is enough information to determine the location and orientation of the tracking array 200 even though two or more markers 212 are not visible to the camera system. For example, if one reflective marker 212 and portions of two different portions of marker lines 222 are visible, this would provide enough information to determine the location and orientation of the tracking array 200. Even two lines that form a unique angle may be used to determine the location and orientation of the tracking array 200.

The tracking array 200 is shown as having three markers 212, three marker lines 222, and having a triangular body 204. More than three markers 212 may also be used in other embodiments. Further, more than three marker lines 222 may also be used in other embodiments. The body 204 may also have other shapes that accommodate the specific application of the tracking array 200.

FIG. 4 illustrates another embodiment of a tracking array that provides the ability to compensate for when part of the tracking array is obstructed. The tracking array 300 is similar to the tracking array 200 of FIG. 4 but does not have the markers 212 of the tracking array 200. The tracking array 300 has a mount 302, body 304, and marker lines 322 similar to those of FIG. 3. The camera system will identify the marker lines 322 and use those to determine the location and orientation of the tracking array 300. One way this may be done is to determine the parameters defining the location of each marker lines 322. Then the location of the intersections between the lines may be determined. These locations may then be used in same algorithm used when the locations of markers 212 are determined by the camera. Other algorithms that identify the marker lines 322 and their locations may also be used to determine the location and orientation of the tracking array 300. For example, a machine learning model may be trained to identify and quantify the marker lines 322 in an image captured by the camera system. Then this data provides the ability to determine the location and orientation of the tracking array 300.

When a portion of the tracking array 300 is obstructed, portion(s) of the marker lines 322 may not be visible to the camera system. In this case, the algorithms may still identify the marker lines 322 as long as a sufficient portion of the marker lines 322 are visible. Further, if a central portion of a marker line 322 is blocked, then two line segments will be seen by the camera system. The algorithms processing the images may identify the different line segments and then determine that they are colinear and hence represent the same marker lines 322. This approach allows for a robust approach to determining the location and orientation of the tracking array 300 even when there may be multiple obstructions. This may be facilitated by using tracking arrays 200 that have marker lines 322 that form unique angles so that each set of lines may be uniquely identifiable (as an equilateral triangle or isosceles triangle have at least two angles the same which creates an ambiguity).

The tracking array 300 is shown as having three marker lines 322 and having a triangular body 304. More than three marker lines 322 may also be used in other embodiments. The body 304 may also have other shapes that accommodate the specific application of the tracking array 300.

Figure 5:
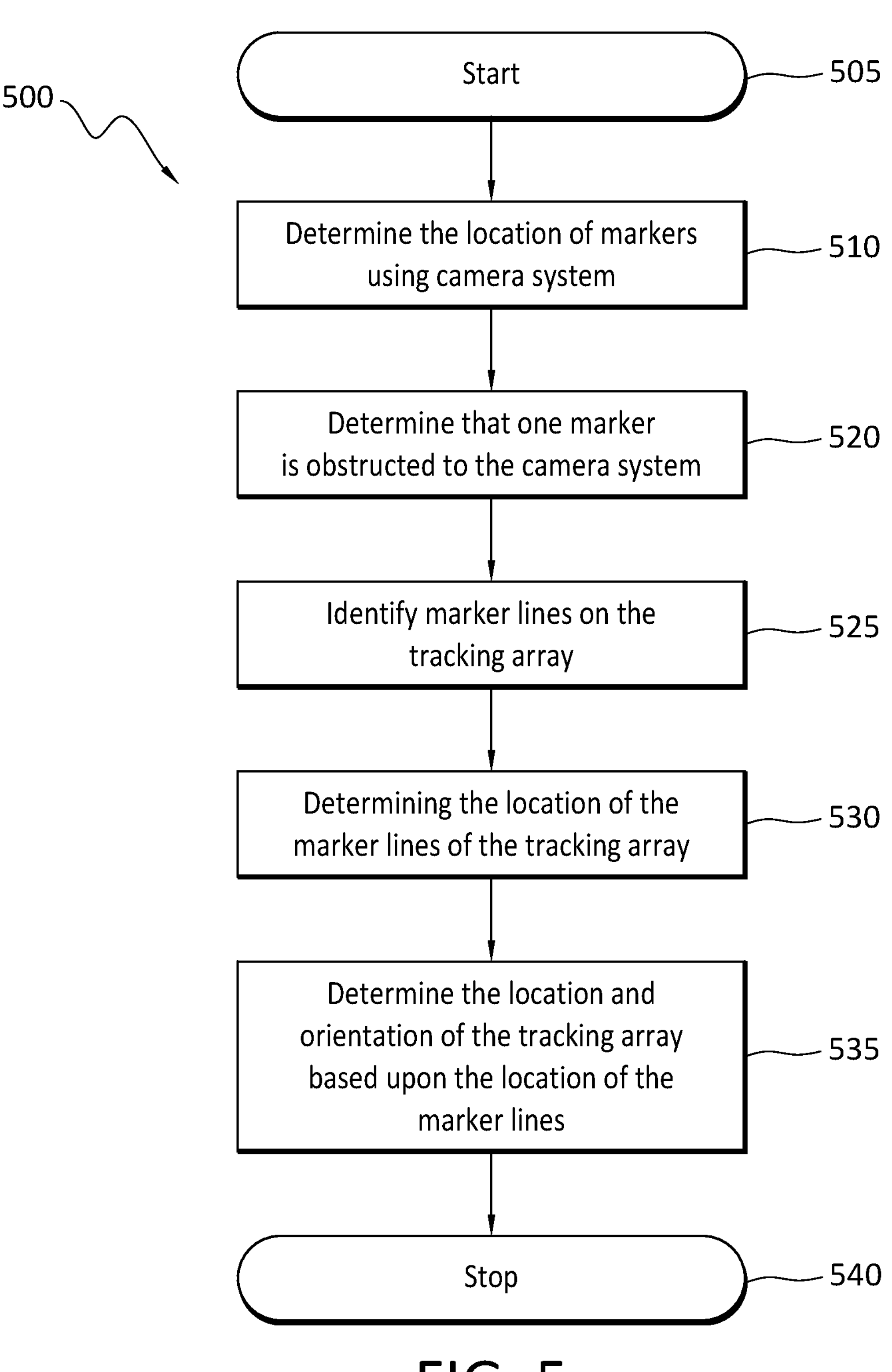
FIG. 5 illustrates a method for determining the location and orientation of a tracking array when a reflective sphere is blocked.

FIG. 5 illustrates a method for determining the location and orientation of a tracking array when a marker is blocked. The method 500 is associated with the tracking array 200 of FIG. 3 that includes both markers 212 and marker lines 222. The method 500 begins at 505 and then determines of location of the markers 212 using the camera system. This is done by taking two stereoscopic images and processing the images to determine the location and orientation 515 of the tracking array 200. This may be accomplished by first performing blob extraction that looks to extract connected components in an image. This may be done by analyzing only pixels that have values over a given threshold value. Next, the method 500 may discard the blobs that are too small or too large. This may be based upon the number of pixels in the blob or the X/Y extent of the blob. Next, the method 500 may compute the center of gravity of the blobs. This may be done by an average or a weighted average of the pixels, where the weight is related to the pixel intensity. The three-dimensional (3D) position of each of the markers 212 may be determined by triangulating its position. For example, this may be done by determining the virtual lines that extend from each sensor's optical center and the blob center and identifying where these virtual lines cross. Other variations of this method and other methods for determining the locations of the markers 212 may also be used instead.

The method 500 then determines the location and orientation of the tracking array 515. This may be done by first taking the locations of the all the markers 212 determined in step 510 and finding a subset of markers 212 that are on the same tracking array 200. In this case this would be three markers 212 that need to be visible to the camera system. In other embodiments, this number may be higher. The subset of related markers 212 may be determined based upon matching their relative locations to the unique and known relative locations of the markers 212 on any trackers that are being used in the CAS. This may be based upon known distances between markers 212 and the angles formed by the markers 212. Next, the method 200 may make the best fit of the subset of measured 3D positions of the markers 212 in the subset and the theoretical markers 212 positions. Then the root mean square (RMS) of the residual distance errors between the measured locations and the theoretical locations is determined. If the RMS errors are above a threshold value, then this potential location determination may be rejected.

Next, the method 500 may determine that one of the markers 212 is obstructed to the camera system 520. After matching all the markers 212 with known tracking array geometries, there may be remaining markers 212 that have not been matched to a known tracking array 200. These unmatched markers may be searched to find partial patterns of tracking arrays that may have a non-visible reflected sphere. For example, a pair of markers may have a distance between them corresponding to a known tracking array.

The method 500 may next identify marker lines 222 on the tracking array that are near the location of the visible markers. The marker lines 222 may be detected in the images captured by the camera system using various methods. For example, the Hough Transform provides the ability to determine the presence of lines in the images. Further, the Hough Transform may also be used to find curved lines or lines with other shapes as well. Another approach is to use binarization followed by skeletonization to detect lines in the images. In yet another example, a pattern matching machine learning model may detect lines in the images. The machine learning model may be for example a deep neural network that is trained with images of a variety of different tracking arrays in a variety of different orientations.

Next, the method 500 determines the location of the detected lines. Again, the Hough Transform or the combination of binarization and skeletonization provides the ability to determine the location of the marker lines near visible markers. It may further be verified that the detected visible marker lines 222 are in a location consistent with the last known location of the tracking array. This may be done by thresholding various differences in the location a position of the detected visible marker lines 222 and the last know location of the visible marker lines 222.

The method 500 then determines the location and orientation of the tracking array 200 based on the location of the visible marker lines 222. A first approach to this would be to determine the 3D positions of the detected lines that intersect at or near the missing marker 212. Then an intersection between the two lines may be determined to then be used to determine the position of the blocked marker 212 as the blocked marker 212 is at known location relative to the intersection of the visible marker lines 222. Then the location of the blocked marker and the locations of the visible markers may be used by the normal processing to determine the location and orientation of the tracking array. As described above, if one reflective marker 212 and portions of two different portions of marker lines 222 are visible, this would provide enough information to determine the location and orientation of the tracking array 200. Even two lines that form a unique angle may be used to determine the location and orientation of the tracking array 200.

In a second approach, pattern matching algorithms provide the ability to match the location of the detected marker lines with the marker lines that are found on the tracking array. Various known pattern matching machine learning models provide the ability to perform this matching and to extract the location and orientation of the tracking array. As discussed above, a pattern matching machine learning model may determine the location of the lines in the images and hence the location and orientation of the tracking array. The machine learning model may be for example a deep neural network that is trained with images of a variety of different tracking arrays in a variety of different orientations.

While the marker lines 222 on the same tracking array 200 are shown as being straight, the visible marker lines 222 may also be curved (in two or three dimensions) or take on other shapes. The various line detection, line estimation, pattern matching techniques described above may be extended to be applied to these other line geometries.

Figure 6:
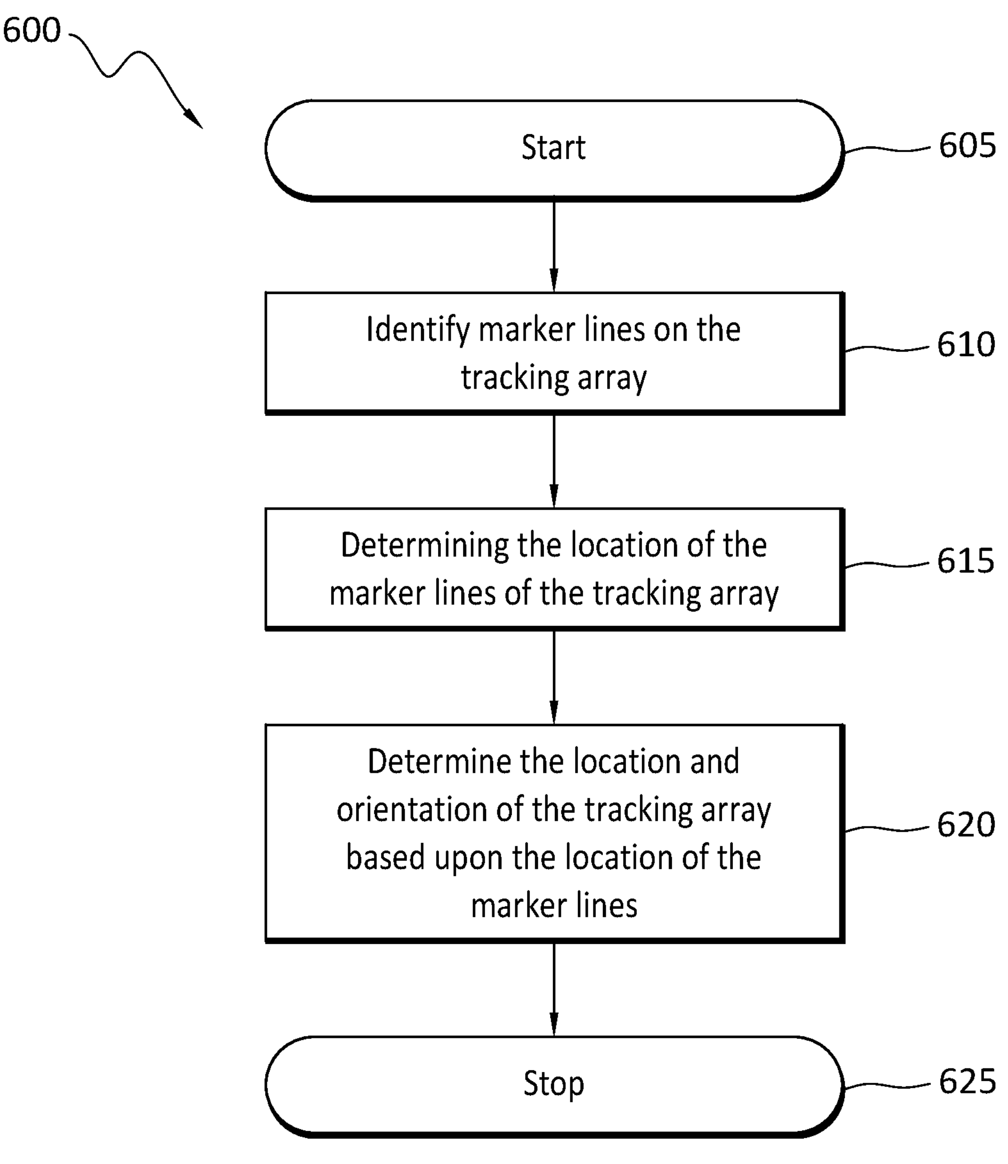
FIG. 6 illustrates another method for determining the location and orientation of a tracking array when a portion of the tracking array is blocked.

FIG. 6 illustrates another method for determining the location and orientation of a tracking array when a portion of the tracking array is blocked. The method 600 is associated with the tracking array 300 of FIG. 4 that includes only marker lines 222. The method 600 begins at 605 and identifies 610 marker lines 322 on the tracking array 300. The marker lines 322 may be detected in the images captured by the camera system using various methods. For example, the Hough Transform provides the ability to determine the presence of lines in the images. Further, the Hough Transform may also be used to find curved lines or lines with other shapes as well. Another approach is to use binarization followed by skeletonization to detect lines in the images.

Next, the method 600 determines the location of the detected lines 615. Again, the Hough Transform or the combination of binarization and skeletonization provide the ability to determine the location of the lines on the tracking array.

The method 600 then determines 620 the location and orientation of the tracking array 300 based on the location of the visible marker lines 322. A first approach to this would be to determine the 3D positions of the detected lines. Then the intersections between the detected lines may be determined. Then location of the intersections of the detected marker lines 322 provide the ability to determine the location and orientation of the tracking array 300. This may be done using the normal processing used with the locations of markers. In another example, two marker lines that form a unique angle may be used to determine the location and orientation of the tracking array 300.

In a second approach, pattern matching algorithms provide the ability to match the location of the detected marker lines with the marker lines 322 that are found on the tracking array 300. Various known pattern matching machine learning models provide the ability to perform this matching and to extract the location and orientation of the tracking array 300.

While the marker lines 322 on the same tracking array 300 are shown as being straight, the visible marker lines 322 may also be curved (in two or three dimensions) or take on other shapes. The various line detection, line estimation, and pattern matching techniques described above may be extended to be applied to these other line geometries The methods 500 and 600 may be performed by the camera system with sufficient processing power. Currently, some camera systems process the received images to detect the markers on the tracking array and to determine the location and orientation of the tracking array while other camera systems may send images to an external processor for processing. In other embodiments, parts or all of the processing of methods 500 and 600 may be performed in processors that are external to the camera system. These processors may be in the CAS system or may be provided external to the CAS system, for example at a central service system or a cloud-based system. Alternatively, the methods 500 and 600 may be carried out by an array tracking system that may include any or all of a camera system, an illumination system, and a processing system.

Figure 7:
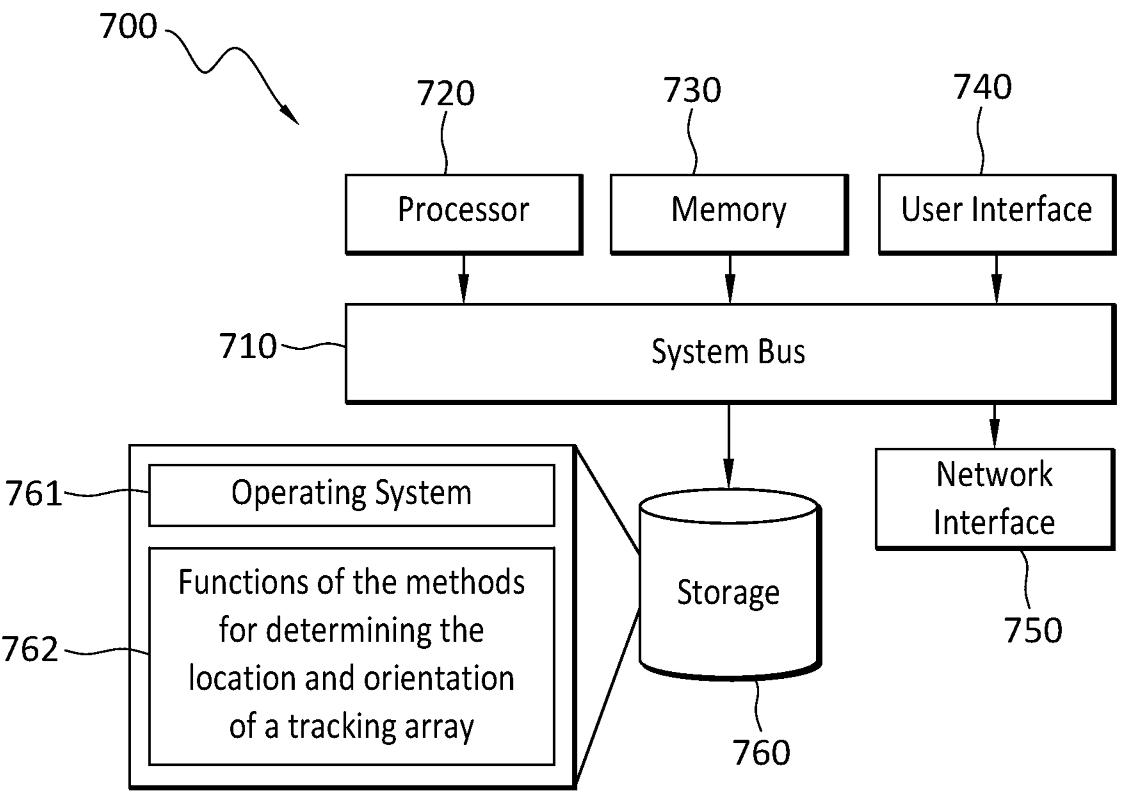
FIG. 7 illustrates an exemplary hardware diagram for implementing the array tracking methods.

FIG. 7 illustrates an exemplary hardware diagram 700 for implementing the array tracking methods 500 and 600. As shown, the device 700 includes a processor 720, memory 730, user interface 740, network interface 750, and storage 760 interconnected via one or more system buses 710. It will be understood that FIG. 7 constitutes, in some respects, an abstraction and that the actual organization of the components of the device 700 may be more complex than illustrated.

The processor 720 may be any hardware device capable of executing instructions stored in memory 730 or storage 760 or otherwise processing data. As such, the processor may include a microprocessor, microcontroller, graphics processing unit (GPU), neural network processor, field programmable gate array (FPGA), application-specific integrated circuit (ASIC), or other similar devices.

The memory 730 may include various memories such as, for example L1, L2, or L3 cache or system memory. As such, the memory 730 may include static random-access memory (SRAM), dynamic RAM (DRAM), flash memory, read only memory (ROM), or other similar memory devices.

The user interface 740 may include one or more devices for enabling communication with a user. For example, the user interface 740 may include a display, a touch interface, a mouse, and/or a keyboard for receiving user commands. In some embodiments, the user interface 740 may include a command line interface or graphical user interface that may be presented to a remote terminal via the network interface 750.

The network interface 750 may include one or more devices for enabling communication with other hardware devices. For example, the network interface 750 may include a network interface card (NIC) configured to communicate according to the Ethernet protocol or other communications protocols, including wireless protocols. Additionally, the network interface 750 may implement a TCP/IP stack for communication according to the TCP/IP protocols. Various alternative or additional hardware or configurations for the network interface 750 will be apparent.

The storage 760 may include one or more machine-readable storage media such as read-only memory (ROM), random-access memory (RAM), magnetic disk storage media, optical storage media, flash-memory devices, or similar storage media. In various embodiments, the storage 760 may store instructions for execution by the processor 720 or data upon with the processor 720 may operate. For example, the storage 760 may store a base operating system 761 for controlling various basic operations of the hardware 700. The storage 760 may include storage 762 that includes software that implements the functions of the methods 500 and 600 for determining the location and orientation of a tracking array in the CAS.

It will be apparent that various information described as stored in the storage 760 may be additionally or alternatively stored in the memory 730. In this respect, the memory 730 may also be considered to constitute a "storage device" and the storage 760 may be considered a "memory." Various other arrangements will be apparent. Further, the memory 730 and storage 760 may both be considered to be "non-transitory machine-readable media." As used herein, the term "non-transitory" will be understood to exclude transitory signals but to include all forms of storage, including both volatile and non-volatile memories.

The system bus 710 allows communication between the processor 720, memory 730, user interface 740, storage 760, and network interface 750.

While the host device 700 is shown as including one of each described component, the various components may be duplicated in various embodiments. For example, the processor 720 may include multiple microprocessors that are configured to independently execute the methods described herein or are configured to perform steps or subroutines of the methods described herein such that the multiple processors cooperate to achieve the functionality described herein. Further, where the device 700 is implemented in a cloud computing system, the various hardware components may belong to separate physical systems. For example, the processor 720 may include a first processor in a first server and a second processor in a second server.

While each of the embodiments are described above in terms of their structural arrangements, it should be appreciated that the invention also covers the associated methods of using the embodiments described above.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications and combinations of the various embodiments can be affected while remaining within the spirit and scope of the invention. Accordingly, the foregoing disclosure, description, and figures are for illustrative purposes only and do not in any way limit the invention, which is defined only by the claims.

What is claimed is:

1. A tracking array tracking system, comprising:

at least one processor; and at least one memory storing instructions, that when executed by the at least one processor, cause the tracking array tracking system at least to:

determine that one marker of a plurality of markers on a tracking array is obstructed to a camera system;

identify a plurality of marker lines on the tracking array;

determine a location and orientation of the marker lines of the tracking array; and determine a location and orientation of the tracking array based upon the location and orientation of the marker lines;

wherein the step of identifying includes identifying, if the camera system has seen at least two marker line segments, a marker line of said plurality of marker lines comprising said at least two marker line segments when the at least two marker line segments are colinear.

2. The tracking array tracking system of claim 1, wherein the instructions further cause the tracking array tracking system at least to:

determine a location of the plurality of markers on the tracking array; and determine a location and orientation of the tracking array based upon the location of the plurality of markers.

3. The tracking array tracking system of claim 1, wherein identifying marker lines includes using a Hough Transform.

4. The tracking array tracking system of claim 1, wherein identifying marker lines includes using a binarization process with a skeletonization process.

5. The tracking array tracking system of claim 1, wherein identifying marker lines includes using a machine learning pattern matching model.

6. The tracking array tracking system of claim 1, wherein determining location and orientation of the tracking array includes:

determining a location of an intersection of marker lines proximate the obstructed reflective element; and determining a location of the obstructed marker based upon the location of the intersection of the marker lines.

7. The tracking array tracking system of claim 1, wherein the marker lines are curved.

8. The tracking array tracking system of claim 1, wherein the marker lines are one of reflective marker lines or active marker lines.

9. A method for tracking a tracking array in a computer aided surgery system, comprising:

determining that one reflective element of a plurality of markers on the tracking array is obstructed to a camera system;

identifying a plurality of marker lines on the tracking array;

determining a location and orientation of the marker lines of the tracking array; and determining a location and orientation of the tracking array based upon the location of the marker lines;

wherein the step of identifying includes identifying, if the camera system has seen at least two marker line segments, a marker line of said plurality of marker lines comprising said at least two marker line segments when the at least two marker line segments are colinear.

10. The method of claim 9, further comprising:

determining a location of the plurality of markers on the tracking array; and determining a location and orientation of the tracking array based upon the location of the plurality of markers.

11. The method of claim 9, wherein identifying marker lines includes using a Hough Transform.

12. The method of claim 9, wherein identifying marker lines includes using a binarization process with a skeletonization process.

13. The method of claim 9, wherein identifying marker lines includes using a machine learning pattern matching model.

14. The method of claim 9, wherein determining location and orientation of the tracking array includes:

determining a location of an intersection of marker lines adjacent the obstructed reflective element; and determining a location of the obstructed marker based upon the location of the intersection of the marker lines.

15. The method of claim 9, wherein the marker lines are curved.

16. The method of claim 9, wherein the marker lines are one of reflective marker lines or active marker lines.

17. A method for tracking a tracking array in a computer aided surgery system, comprising:

identifying a plurality of marker lines on the tracking array;

determining a location and orientation of the marker lines of the tracking array; and determining a location and orientation of the tracking array based upon the location and orientation of the marker lines;

wherein the step of identifying includes identifying, if the camera system has seen at least two marker line segments, a marker line of said plurality of marker lines comprising said at least two marker line segments when the at least two marker line segments are colinear.

18. The method of claim 17, wherein identifying marker lines includes using a Hough Transform.

19. The method of claim 17, wherein identifying marker lines includes using one of a binarization process with a skeletonization process and a machine learning pattern matching model.

20. The method of claim 17, wherein determining location and orientation of the tracking array includes:

determining locations of intersections of marker lines of the tracking array; and computing the location and orientation of the tracking array based upon the locations of the intersections of the marker lines of the tracking array.

21. The method of claim 17, wherein the marker lines are one of reflective marker lines or active marker lines.

* * * * *